(12) United States Patent
Staunton et al.

(10) Patent No.: US 6,226,552 B1
(45) Date of Patent: May 1, 2001

(54) NEUROMUSCULAR ELECTRICAL STIMULATION FOR PREVENTING DEEP VEIN THROMBOSIS

(75) Inventors: Douglas A. Staunton; Richard F. Huyser, both of Kalamazoo; Harry A. Wellons, III, Portage; Mark A. Wasserman, Delton; Jerry A. Culp, Kalamazoo; Patrick J. Del Medico, Portage; Donald W. Malackowski, Schoolcraft, all of MI (US)

(73) Assignee: Stryker Instruments, Kalamazoo, MI (US)

( * ) Notice: Subject to any disclaimer, the term of this patent is extended or adjusted under 35 U.S.C. 154(b) by 0 days.

(21) Appl. No.: 09/293,864

(22) Filed: Apr. 16, 1999

Related U.S. Application Data
(60) Provisional application No. 60/082,248, filed on Apr. 17, 1998.

(51) Int. Cl.[7] .................................................. A61N 1/32
(52) U.S. Cl. ............................................................ 607/72
(58) Field of Search ................................. 607/2, 46, 48, 607/49, 62, 63, 68, 70, 72, 74, 115, 149, 152, 153; 600/372, 382, 384, 386, 390, 391

(56) References Cited

U.S. PATENT DOCUMENTS

| | | | |
|---|---|---|---|
| 3,364,929 | * | 1/1968 | Ide et al. . |
| 4,770,328 | * | 9/1988 | Dickhudt et al. . |
| 5,146,920 | * | 9/1992 | Yuuchi et al. ........................ 607/63 |
| 5,158,080 | * | 10/1992 | Kallok .................................. 607/42 |
| 5,643,331 | * | 7/1997 | Katz . |
| 5,782,893 | * | 7/1998 | Dennis, III ............................ 607/48 |

* cited by examiner

Primary Examiner—Kennedy Schaetzle
(74) Attorney, Agent, or Firm—Howard & Howard

(57) ABSTRACT

A neuro-muscular electrical stimulation system provides a series of electrical pulses to instigate muscle twitch to aid in preventing the occurrence of deep vein thrombosis. The duration and duty cycle of the electrical pulses provided to a patient's muscle tissue is controlled to instigate muscle twitch without causing tetanic muscle contractions. The system preferably includes a single electrode that is placed upon each calve of a patient. The electrical stimulator device includes a unique housing and circuit board arrangement that facilitates easy assembly without requiring any soldering connections between the circuit board, a power source and electrical leads that are utilized to provide signals to the electrodes that are placed on the patient. The circuit board preferably is made from a slightly resilient plastic material that is flexed from a disconnected position into an electrically connected position upon assembly of the stimulator device.

34 Claims, 7 Drawing Sheets

NEUROMUSCULAR ELECTRICAL STIMULATION FOR PREVENTING DEEP VEIN THROMBOSIS

This application claims benefit to Provisional Application 60/082,248 filed Apr. 17, 1998.

FIELD OF THE INVENTION

This invention generally relates to a system for preventing deep vein thrombosis including an electronic stimulator that delivers electrical pulses to stimulate muscle twitch.

BACKGROUND OF THE INVENTION

Deep vein thrombosis (DVT) is a common and significant complication of surgeries that require anesthetizing the patient. Studies have shown that the risk for DVT occurrence in orthopedic patients having lower extremity surgeries such as total knee arthroplasty, total hip arthroplasty, and hip fracture repair, may be as high as seventy percent. The clinical manifestations of DVT can include tenderness, edema, and discoloration; however, these physical findings typically are present in only twenty-three to fifty percent of the patients with DVT so there often is no visible warning of DVT complications. Post-thrombotic syndrome from DVT may arise in five to ten percent of DVT patients with symptoms presenting in the form of chronic edema and ulcers of the lower extremities.

The most significant complication arising from DVT is pulmonary embolism. Pulmonary emboli are recognized as the most common fatal complication following surgery or trauma involving the lower extremities. Pulmonary emboli (PE) are the principal or major contributing factor in the cause of death in approximately fifteen to thirty percent of all hospitalized patients and result in an estimated 50,000 to 100,000 deaths per year. The rates of clinically significant pulmonary embolism in orthopedic patients have been reported to be as high as twenty percent with a one to three percent incidence of fatality. This is significant as otherwise successful surgical procedures can result in a loss of life, often with little or no warning.

The generally accepted theory on the formation of thrombi includes vessel wall damage, hyper-coagulability, and stasis. It is believed that stasis can lead to the development of vessel wall damage and hyper-coagulability.

Deep vein thrombi predominantly form in the deep veins of the legs which are surrounded by the gastrocnemius and the soleus muscle groups. DVTs initially form distally in the deep veins and grow proximally prior to their potential release as emboli. Contraction of the gastrocnemius and the soleus muscle groups activate the body's "skeletal muscle pump" by compressing the deep veins and mechanically pushing blood back toward the heart. The blood flow is unidirectional as veins contain valves which permit the flow of blood in only one direction (towards the heart). The action of the "skeletal muscle pump" is a process which occurs nearly continuously in ambulatory people. Even while sleeping, a person's body periodically shifts and muscles twitch which activate the "skeletal muscle pump."

During surgery, the body's "skeletal muscle pump" can be compromised due to the effects of general anesthesia and paralytic agents administered to facilitate, for example, intubation. This compromise of the "skeletal muscle pump" can lead to stasis of blood in the deep veins, formation of deep vein thrombi, and ultimately the formation of emboli. This situation is further aggravated as surgical patients tend to be non-ambulatory for a significant period of time after surgery. Without ambulation, the "skeletal muscle pump" is only marginally effective. Accordingly, prevention of the blood stasis in the deep veins during surgery and subsequent augmentation of blood flow in the post-surgical period represents a very important window of opportunity for preventing the formation of DVTs.

Many techniques have been proposed and utilized in an attempt to prevent the formation of thrombi. In particular, pharmacological and mechanical modalities have been studied.

Pharmacological efforts have been primarily targeted at blood hypercoagulability using either anti-platelet drugs or anti-coagulant blood thinners such as heparin and coumadin. These pharmacological techniques have been at least partially successful in preventing DVTs. Studies have shown that DVT rates can be decreased by over fifty percent depending on the specific drug utilized, surgery, and administration protocol. Such drugs are effective because they cause blood thinning and prevent coagulation. Therefore, physicians are not particularly enthusiastic about using these drugs as they can cause bleeding complications, they are expensive, they are logistically complicated to use, and the general trend is moving away from the use of such drugs.

Alternatively, stasis can be prevented by the use of mechanical devices such as Sequential Compression Devices (SCDs) that compress or squeeze a patient's legs to force blood flow towards the heart, foot pumps that rapidly compress the plantar tendon to push blood from the arch area, or compression stockings that provide support to blood vessel walls. These devices have met with success and have helped to decrease DVT rates by approximately sixty to eighty percent.

Commercially available devices, however, are fraught with drawbacks. They typically are bulky and impose a considerable burden on the hospital staff. Patients are less inclined to ambulate while using these devices because they typically are burdensome to remove and reapply. Early and frequent ambulation following surgery is strongly correlated with quicker overall recovery and decreased risk of DVT/ PE. Conventional devices are expensive and difficult to use during surgery. Moreover, since conventional devices are durable goods owned and maintained by the hospital, they are not suited for post-operative home care, during which studies have shown that active DVT prophylaxis is still necessary. Additionally, patient compliance is typically very poor when using the mechanical devices as they are uncomfortable, interfere with sleep and may cause accumulation and stagnation of perspiration, resulting in unpleasant odors.

Electrical stimulation of muscle groups of the lower extremities has been shown to be effective for preventing DVT. A number of electrical stimulation devices exist and have been used to cause muscle contractions. Included in this class of electrical stimulating devices are the transcutaneous electrical nerve stimulators commonly known as TENS units. TENS units have been primarily utilized in post-surgical or non-surgical situations for the reduction or minimization of pain. The TENS units are designed to block pain at the level of the nerve endings.

A more recent development in the use of electrical stimulation to prevent DVT has been the use of neuro-muscular electrical stimulation (NMES) on the lower extremities to promote venous return of blood as disclosed in U.S. Pat. No. 5,556,422, issued Sep. 17, 1996. The NMES device uses tetanic frequency stimulation to cause dorsiflexion neutral inversion/eversion muscle contraction which is utilized for promoting venous blood return from the deep veins in a patient's leg. The dorsiflexion and stretching stimulated by the repeated application of an electrical current at a predetermined, regular interval has been found to increase the blood flow in deep leg veins. This type of electrical stimulation causes significant, sustained muscle contraction and movement about the ankle joint and, therefore, is not useful during surgery. The substantial movement caused by the dorsiflexion may be adverse in a surgical situation wherein a particular surgical procedure requires the patient to be virtually immobile during the procedure. An additional drawback of this type of stimulation is that it can be painful and fatiguing to the patient.

Accordingly, it would be desirable to have a device and method that prevents DVT, which can be utilize in the intra-operative setting, the post-operative setting, and/or therapeutic settings. This invention meets that need and overcomes the disadvantages of the prior art devices described above.

SUMMARY OF THE INVENTION

In general terms this invention is a system that utilizes neuro-muscular electrical stimulation to prevent the occurrence of deep vein thrombosis. A system designed according to this invention includes two electrode pads that are adapted to be placed on a selected portion of a patient's body, such as the posterior of the lower legs. An electrical stimulator device provides a series of electrical pulses that are transferred through the pads to the patient's muscles. The pulses from the stimulator have a specific timing and wave form arrangement such that the patient's muscles are stimulated to twitch but not to cause movement of the limb with tetanic contractions.

In the preferred embodiment, the stimulator device provides a series eight electrical pulses that each have a two hundred microsecond duration and are spaced apart by 200 milliseconds. At the end of the eight pulses, no stimulation is provided for a period of approximately forty-three seconds. At the end of the forty-three second pause, the eight pulses are again repeated. Further, the eight pulses preferably are provided using increasing intensity through the first five pulses, with the fifth pulse being at full strength. The first pulse preferably provides approximately forty percent of the desired stimulation intensity. Each of the second through fifth pulses preferably includes a fifteen percent increase in intensity. The fifth through eight pulses all preferably are at one hundred percent intensity based upon a currently desired stimulation setting.

The various features and advantages of this invention will become apparent to those skilled in the art from the following description of the currently preferred embodiment. The drawings that accompany the detailed description can be briefly described as follows.

BRIEF DESCRIPTION OF THE DRAWINGS

FIG. 1A illustrates a preferred feature of a selected portion of the embodiment of FIG. 1.

DETAILED DESCRIPTION OF THE PREFERRED EMBODIMENT

Figure 1:
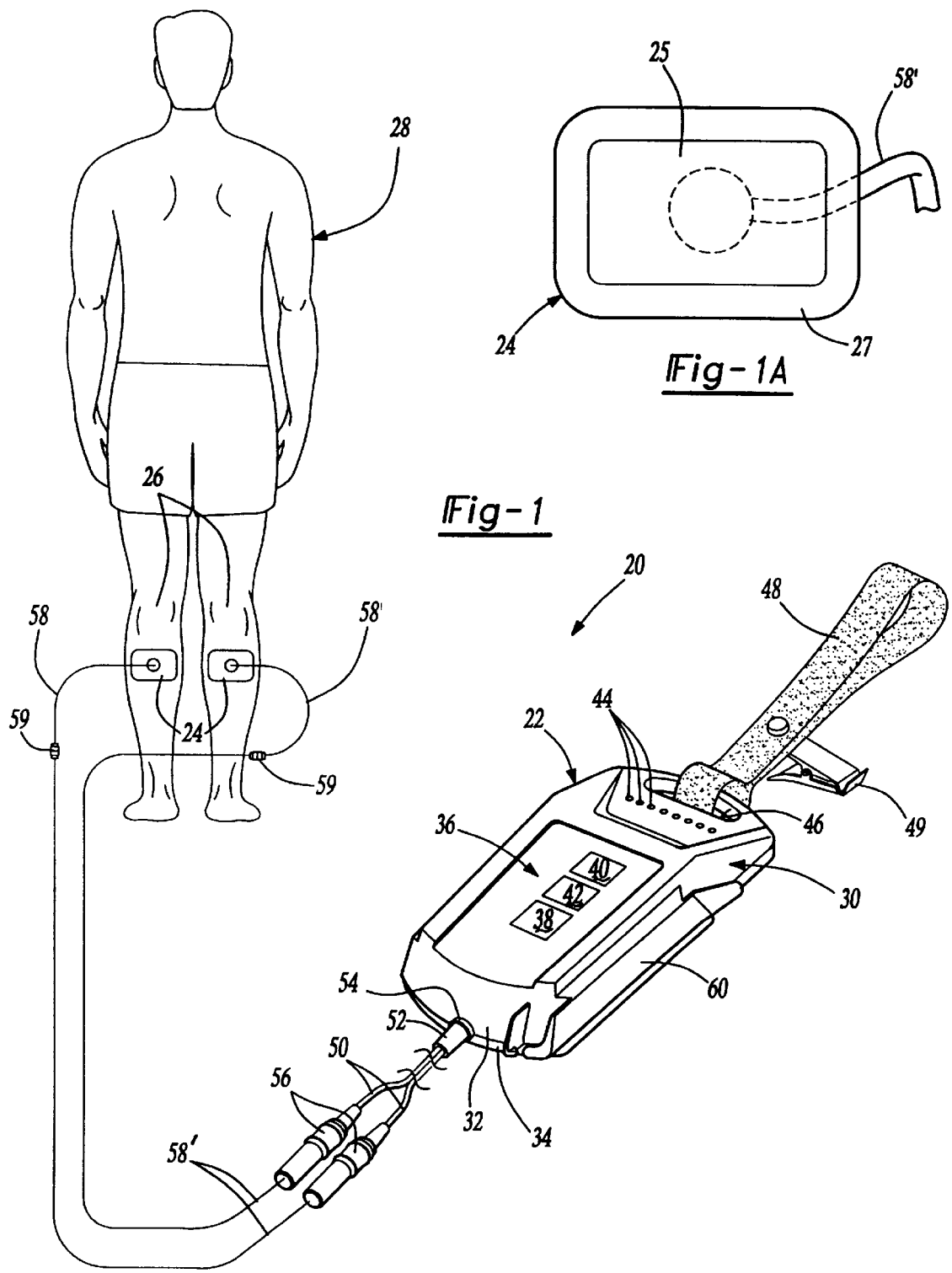
FIG. 1 diagrammatically illustrates a system designed according to this invention.

FIG. 1 illustrates a neuro-muscular electrical stimulation system 20 including a stimulator device 22 and a pair of electrode pads 24 that are attached to the lower posterior of the legs 26 of a patient 28. As seen in FIG. 1A, the pads 24 preferably include an adhesive, conductive gel 25 and a backing 27 that has a larger dimension than the gel 25. The backing 27 provides a waterproof seal around the gel 25 when the pads 24 are placed against the patient's skin. The system 20 preferably provides electrical stimulation pulses to the gastrocnemius and soleus muscles in the patient's calves to cause twitching of the muscles without causing muscle tetany. The stimulation of the muscles in the lower legs of the patient 28 enhances blood through the lower extremities and reduces the risk of deep vein thrombosis (DVT).

The following description will include a description of the preferred arrangement of components that make up the system 20. Following the description of the components, the operation of the system 20 will be described.

SYSTEM COMPONENTS

The stimulator device 22 preferably includes a plastic housing 30 that is made from a first housing portion 32 and a second housing portion 34. The two housing portions preferably are ultrasonically welded together during the assembly process so that they cannot be separated. Further, joining the first housing portion 32 and the second housing portion 34 in this manner provides a splash-proof housing for the internal components of the stimulator device 22.

Figure 2:
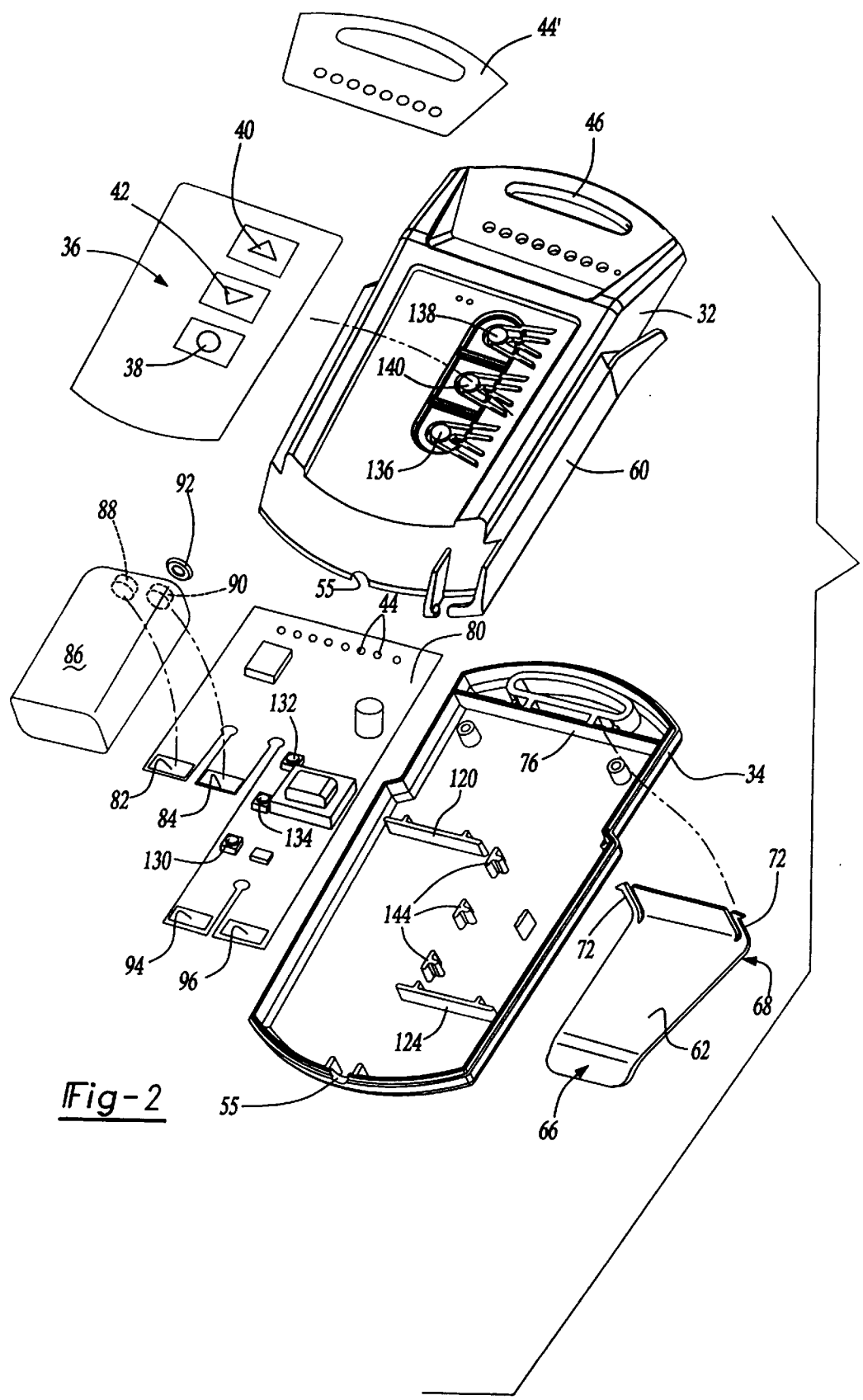
FIG. 2 is an exploded view diagrammatically and schematically illustrating selected components of a stimulator device designed according to this invention.
Figure 4:
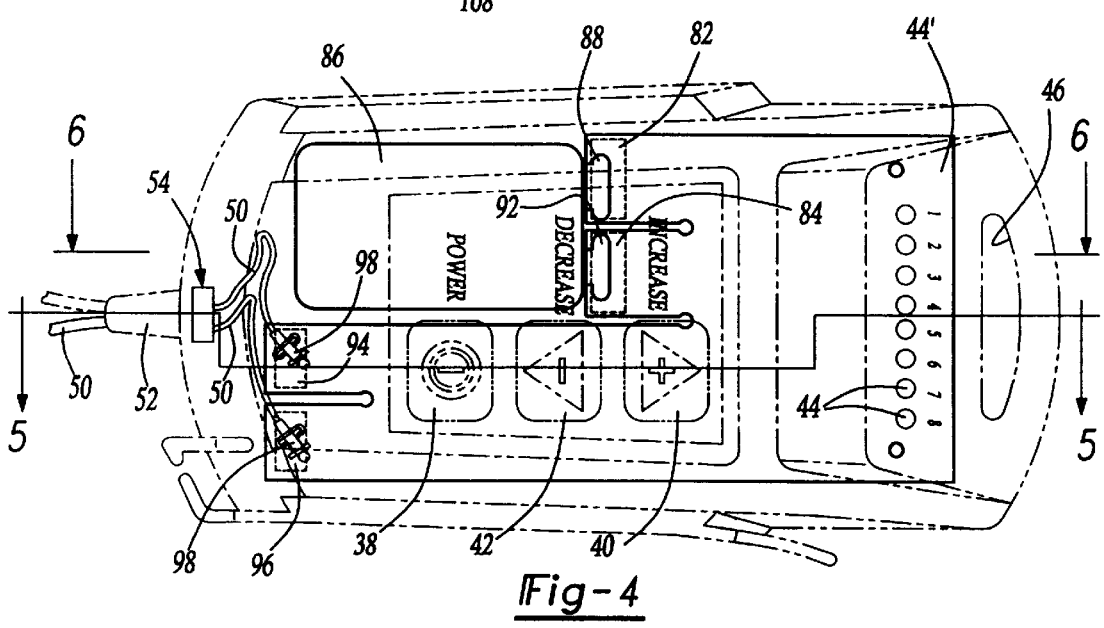
FIG. 4 is a top elevational view showing the components of FIG. 3 in an assembled condition.

As best seen in FIGS. 1, 2 and 4, the first housing portion 32 preferably supports a user interface portion 36, which preferably is an adhesive label secured onto the first housing portion 32. The operator interface 36 preferably includes a power button 38 and stimulation level adjustment buttons 40 and 42. In the illustrated example, the button 40 is utilized to increase the stimulation provided by the device 22 while the button 42 can be used to decrease the intensity of the stimulation as will be described in more detail below.

A plurality of indicators 44 provide a visible indication regarding the operation of the stimulator device 22 as will be described in more detail below. In the preferred embodiment, the indicators 44 are light emitting diodes enclosed within the housing 30. As can be appreciated from FIG. 2, the preferred embodiment includes a face plate 44' that includes indicia to help a user interpret the status information provided through the indicators 44.

A strap support 46 preferably is formed in the housing 30 near the indicators 44. A carrying strap 48 preferably includes a hook and loop fastening portion that allows the strap to be hung upon a patient's bed, for example. The strap 48 is also useful for carrying about the stimulator device 22 as a patient moves about during a recovery from surgery, for example. A badge-type clip 49 is riveted through the strap 48 and is useful for attaching the stimulator device 22 to a patient's hospital gown or bed clothes.

At the opposite end of the housing 30 a set of electrical leads 50 extend outward and away from the housing 30. The preferred embodiment includes a wire harness 52 that is received within an opening 54 on the housing 30. The opening 54 preferably is formed by mating notches 55 on the first housing portion 32 and the second housing portion 34, respectively. The wire harness 52 preferably is made from a generally flexible, elastomeric material. The wire harness 52 preferably is configured to snugly fit within the opening 55 to prevent any fluids or other contaminants from entering into the interior of the housing 30. Although the first housing portion 32 and second housing portion 34 are ultrasonically welded together, the opening 55 and the wire harness 54 do not provide a water-tight seal around the entire perimeter of the housing 30. Therefore, the preferred embodiment of the housing 30 provides splash-proof protection for the interior components but is not necessarily completely waterproof.

Each of leads 50 preferably terminates in a connector 56 that receives the end of wires 58, which are coupled to the pads 24 or sterile extension wires 58' using connectors 59 at opposite ends. The connectors 56 facilitate changing pads 24 and utilizing sterile extension wires 58' depending on the needs of a particular situation. For example, when a patient is recovering post-operatively only the wires 50, which are permanently attached to the stimulator device 22, will be employed. When a patient is in surgery, however, longer sterile extension wires 58' may be needed to exit the sterile field. Additionally, the pads 24 preferably are replaced as often as once per week and, therefore, the connectors 56 facilitate easily utilizing the stimulator device 22 with a plurality of the pads 24.

The housing 30 preferably also includes a wire support 60 that facilitates wrapping portions of the leads 50 for more convenient placement while using or storing the system 20.

Figure 5:
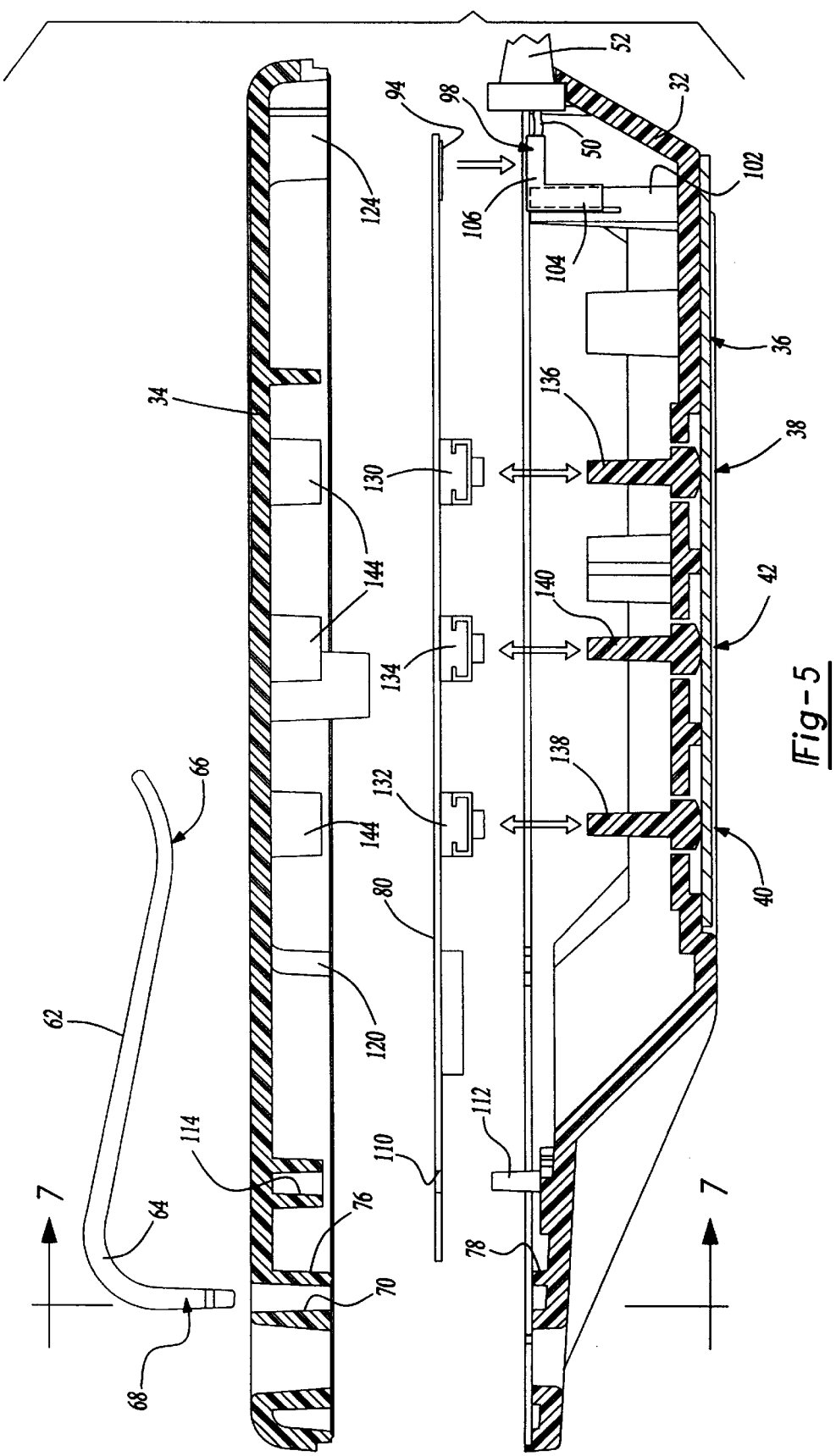
FIG. 5 is a cross-sectional illustration taken along the lines 5—5 in FIG. 4.
Figure 7:
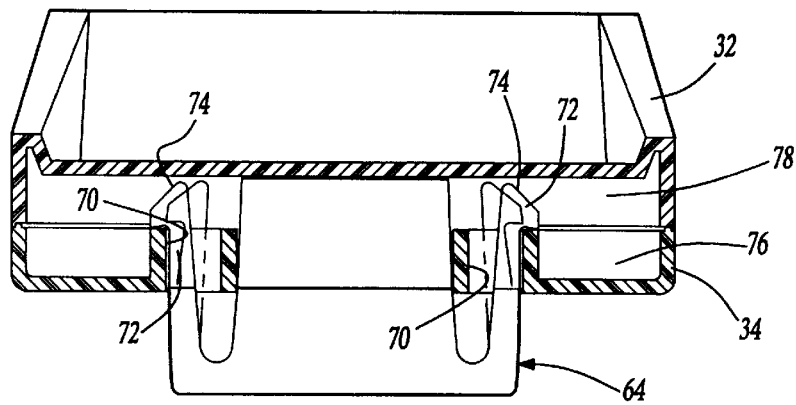
FIG. 7 is a cross-sectional illustration taken along the lines 7—7 from FIG. 5.

In addition to the carrying strap 48 and badge-type clip 49, the preferred embodiment of the housing 30 includes a clip 62 that is received against an outside face of the second housing portion 34. A first portion as best seen in FIGS. 2, 5 and 7, the clip 62 includes a cantilever portion 64 and a distal end 66. When an insert portion 68 of the clip 62 is received within a corresponding channel 70 on the housing 30, the cantilever portion 64 biases the distal end 66 of the clip against the outside face of the second housing portion 34.

The insert portion 68 preferably includes two tongues 72 that each have a ramped surface 74 to facilitate inserting the clip portion 68 into the channel 70. The clip 62 preferably is made of a relatively rigid plastic material and the tongues 72 preferably are positioned to be biased into an engaging position with the channel 70 to maintain the clip 62 in position relative to the housing 30. The clip 62 facilitates carrying the stimulator device about while a patient is walking, for example.

The channel 70 preferably is formed on the second housing portion 34. The channel 70 preferably is separated from the interior of the housing 30 by walls 76 and 78 on the second housing portion 34 and the first housing portion 32, respectively. Therefore, the interior components supported within the housing 30 are isolated from outside contaminants that would otherwise potentially enter in through the channel 70.

The preferred embodiment includes a minimum number of separate components that must be assembled into the housing 30 to make the stimulator device 22. This invention includes specifically designed and arranged components that greatly enhance quick, effective and economic assembly and manufacture. As can be appreciated from FIGS. 2 through 6, a single circuit board 80 is supported within the housing 30. The circuit board 80 preferably supports all of the electronics responsible for generating the pulse signals that are utilized for the DVT prevention regimen. The preferred embodiment of the circuitry will be described below.

The circuit board 80 includes a first set of connection terminals 82 and 84 that are utilized to make electrical contact with a power source 86. In the preferred embodiment, the power source 86 comprises a 9 volt alkaline battery. The connection terminals 82 and 84 have a size and shape that renders them capable of making electrical contact with a female terminal 88 and a male terminal 90 on the battery 86. The preferred embodiment includes an adapter 92 that is received over the male terminal 90 of the battery 86. The adapter 92 has an outside dimension that is equal to the outside dimension of the female terminal 88. Having equal outside dimensions for the female terminal 88 and the male terminal 90 ensures proper electrical coupling with the connection terminals 82 and 84.

Additional electrical coupling terminals 94 and 96 preferably are provided at an end of the circuit board 80 that is distal from the indicators 44. The terminals 94 and 96 are utilized to make a connection with the leads 50 so that signals provided by the components supported by the circuit board 80 result in the appropriate stimulation of the patient's muscles through the pads 24.

The leads 50 preferably terminate in connectors 98. The first housing portion 32 preferably includes support posts 102 that receive and support the connectors 98 to facilitate electrical coupling with the terminals 94 and 96. The connectors 98 preferably include a first portion 104 that is received on the posts 102 and a second portion 106 that extends generally perpendicularly from the first portion 104 after bending over the edge of the support posts 102. As can best be appreciated from FIGS. 5 and 6, the terminals 94 and 96 preferably make direct contact with the second portions 106 of each of the connectors 98 when the device is assembled.

The preferred method of assembling the components of the stimulator device 22 includes preforming the housing portions 32 and 34 and the clip 62 from a plastic material using a conventional molding process. Since the power source 86 preferably is a conventional 9 volt battery, that can be acquired readily. The leads 50 preferably are provided with the connectors 98 and placed within the wire harness 52. The circuit board 80 preferably is premanufactured in the sense that it already contains all of the circuit elements to be described below.

Figure 3:
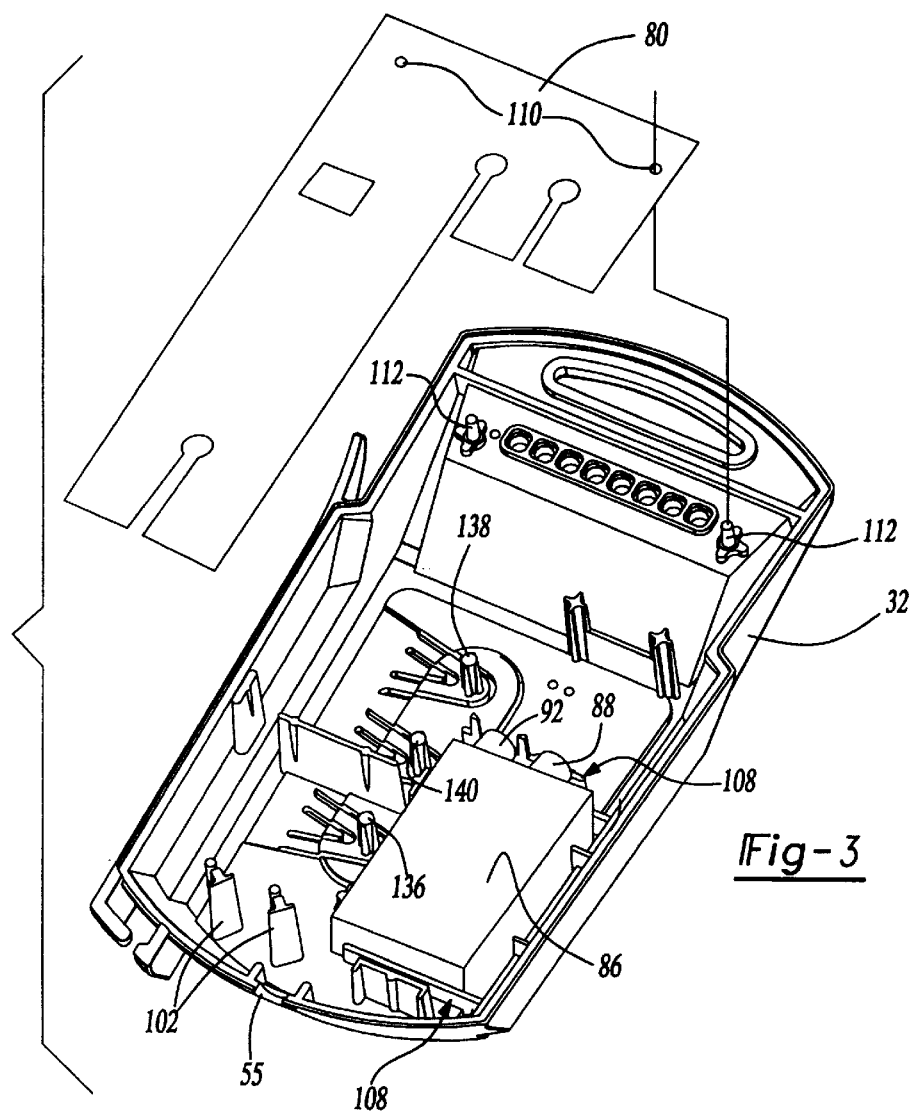
FIG. 3 illustrates, from another perspective, selected components from the illustration of FIG. 2.

The assembly process preferably includes turning the first housing portion 32 "face-down" as illustrated in FIG. 3. The adapter 92 is secured on the male terminal 90 and the battery 86 is then placed within a battery receptor portion 88 on the first housing portion 32 so that the battery 86 is maintained in a desired position. Next, the connectors 98 preferably are positioned on the posts 102, bent over the edge of the posts 102 and the wire harness 52 is placed within the notch 55 on the first housing portion 32. Next, the circuit board 80 is set onto the first housing portion 32 such that a pair of openings 110 through the circuit board 80 are received over position posts 112.

Figure 6:
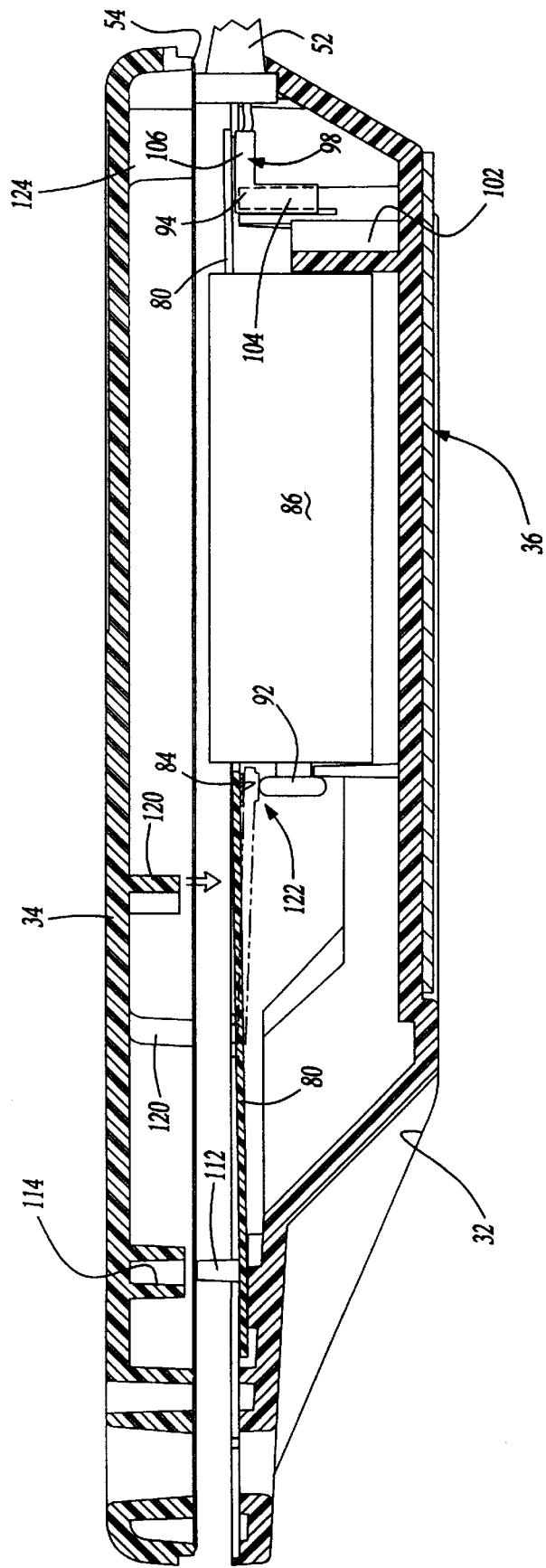
FIG. 6 is a cross-sectional illustration taken along the lines 6—6 in FIG. 4.

As illustrated in FIG. 6, at this stage of the assembly process, the end of the circuit board 80 that supports the indicators 44 is in contact with the first housing portion 32 while the opposite end supporting the connectors 94 and 96 is supported against and in contact with the connectors 98. The circuit board 80 preferably is biased slightly within the housing portion 32 so that there is some spacing between the connection terminals 82 and 84 and the terminals 88 and 90 on the battery 86.

As the second housing portion 34 is moved into position against the first housing portion 32, the support posts 112 are received within corresponding openings 114 on the second housing portion 34. The wire harness 52 is received by the notch 55 on the second housing portion 34 so that the wire harness 52 is snugly engaged within the opening 54. A projection 120 is provided on the interior of the second housing portion 34. This projection 120 contacts the circuit board 80 as the second housing portion 34 is moved into position against the first housing portion 32. The projection 120 biases or moves the circuit board 180 against the bias from the initial position and causes electrical contact between the battery terminals 88 and 90 and the connection terminals 82 and 84. This is illustrated in phantom at 122 in FIG. 6. Another projection 124 ensures the connection between the terminals 94 and 96 and the connectors 98. When the two housing portions are secured together, the electrical connection between the terminals 82 and 84 and the battery terminals and the connections between the terminals 94 and 96 and the connectors 98 are secured. The circuit board 80 preferably is made of a generally stiff yet flexible plastic material to accommodate the flexing necessary to make the connections during assembly.

Therefore, this invention provides a relatively simple and efficient way of making electrical connections that are secure and reliable throughout the lifetime of the stimulator device 22. Moreover, manufacturing economies are maximized since no soldering is required to make secure electrical connections.

The stimulator device 22 is intended to be disposable. Since a single battery 86 is provided within the housing 30, the expected lifetime of the stimulator device 22 is approximately six weeks.

As can be best seen in FIGS. 2 and 5, the circuit board 80 supports switches 130, 132 and 134, respectively. These are the mechanical switches that are responsible for communicating a user's intentions to the functional portions of the electronics supported on the circuit board 80. In the illustrated example, the switch 130 is the power switch that enables the user to turn the stimulator device 22 on or off. Although the user presses on the indication 38 on the cover 36, the switch 130 is activated by a switch activator 136 that is formed as a part of the first housing portion 32.

Similarly, switch activators 138 and 140 are provided for activating the switches 132 and 134, respectively. Switches 132 and 134 are used to selectively adjust the intensity of electrical pulses experienced by the muscles in the vicinity of the pads 24.

The second housing portion 34 preferably includes a plurality of switch backing members 144 that project away from the interior surface of the second housing portion 34. As can be best appreciated from FIG. 5, the switch backing members 144 abut against the side of the circuit board 80 behind the switches 130–134. The switch backing members 144 ensure that the action of moving one of the switch actuators 136–140 will not deflect the circuit board 80 within the housing 30, but instead will result in proper operation of the switches and the corresponding operation of the device.

SYSTEM ELECTRONICS

Figure 8:
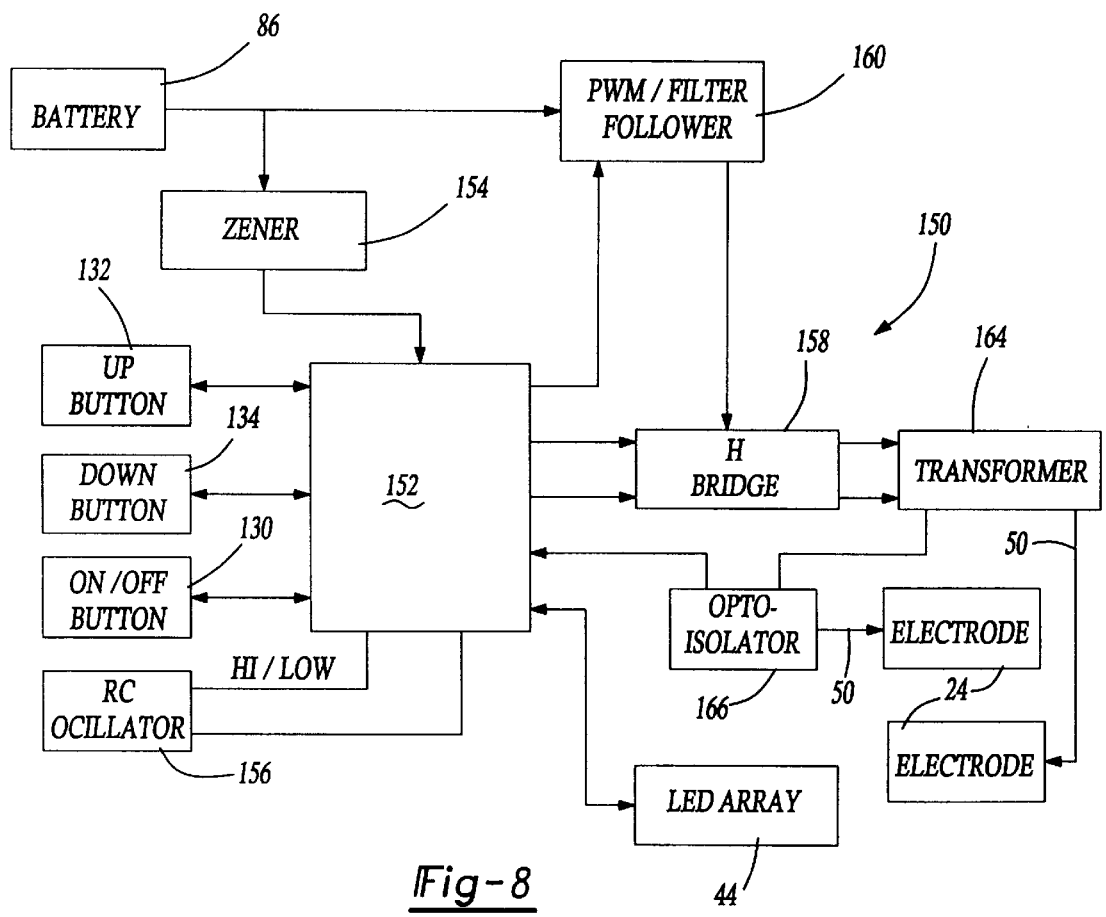
FIG. 8 is a block diagram illustrating a preferred arrangement of circuit components for the stimulator device.
Figure 9:
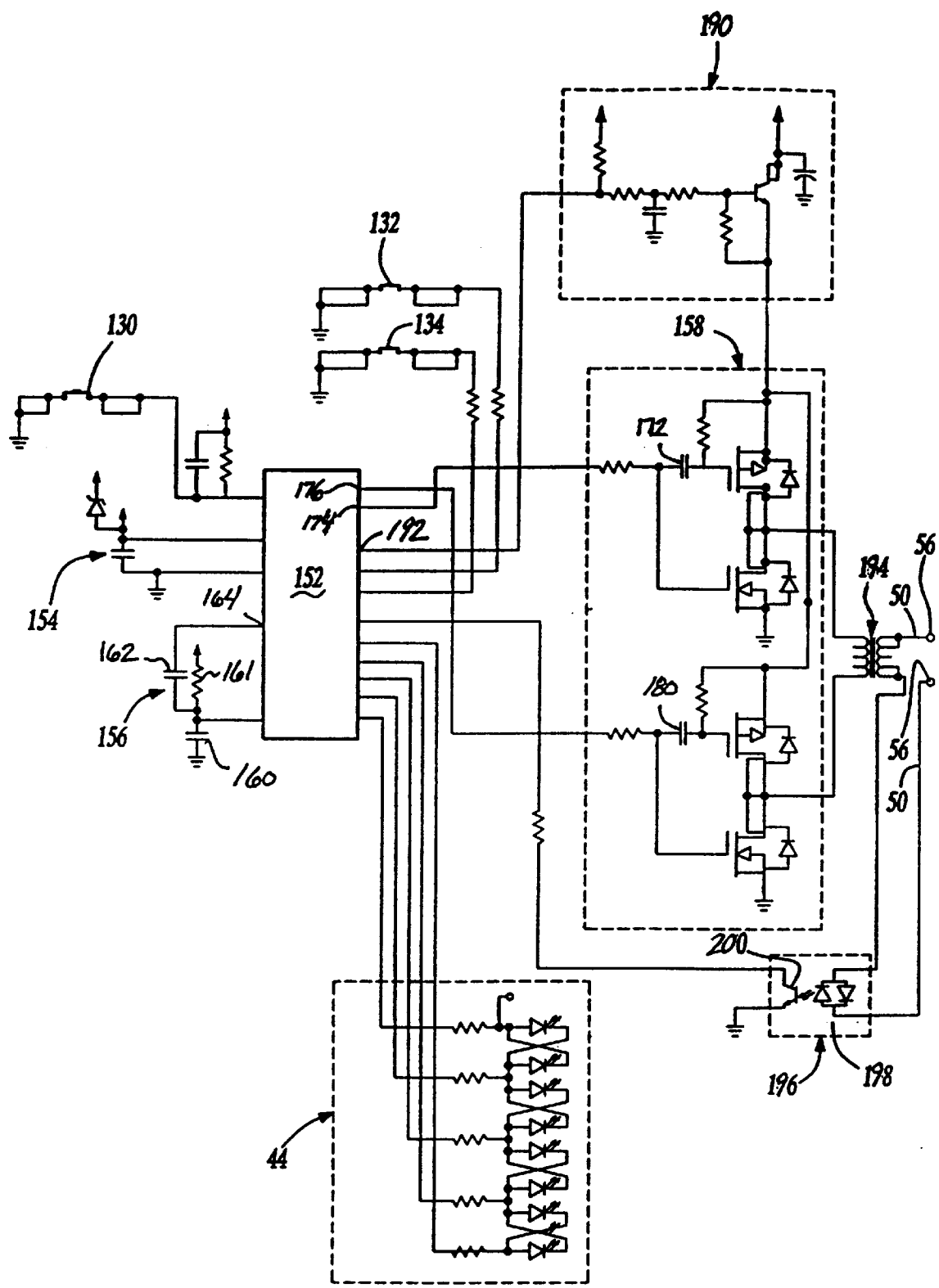
FIG. 9 is a schematic diagram illustrating the preferred arrangement of circuit components.

The circuit board 80 preferably supports all of the electronics responsible for generating the signals that result in the neuromuscular electrical stimulation as part of the DVT prevention regimen that is available by utilizing this invention. FIG. 8 is block diagram that illustrates the preferred arrangement of electronics while FIG. 9 is a more detailed schematic diagram showing example components utilized to operate the stimulator device 22. It should be noted that the battery 86 and electrodes 24 preferably are not supported by the circuit board 80. Otherwise, the preferred embodiment includes supporting all of the remaining components schematically illustrated in FIGS. 8 and 9 on the circuit board 80.

The circuitry 150 preferably includes an electronic controller 152, which may be a conventional microprocessor or other standard components. The electronic controller 152 receives power from the battery 86 through a zenor diode arrangement 154, which ensures the proper operating voltage for the electronic controller 152.

The power switch 130 preferably is activated to reset the electronic controller 152 each time that the switch 130 is activated. In the preferred embodiment, the electronic controller 152 remains running at all times and is simply reset into one of two modes depending on the state of the controller prior to the switch 130 being activated. The electronic controller 152 preferably includes a static bit that alternates between an "off" and an "on" state. Each time that the switch 130 is activated, the controller 152 looks at the status of the static bit and changes the operational mode of the controller to the opposite of the current mode. For example, when the electronic controller 152 is in a sleep mode and the switch 130 is activated, the electronic controller switches to a running mode. The next time that the switch 130 is activated, the electronic controller 152 switches back into the sleep mode. Providing an alteration between a running mode and sleep mode serves the purpose of conserving the energy available from the battery 86.

An oscillator circuit portion 156 is utilized by the electronic controller 152 as a time reference to generate pulse signals that are supplied to an H bridge circuit portion 158. The electronic controller 152 preferably operates as a dual-speed microprocessor utilizing the oscillator circuit portion 156. The preferred embodiment includes a first capacitor 160 and a resistor 161. A second capacitor 162 preferable is provided, which is effectively connected to an output 164. When the output from the pin 164 of the controller 152 has a high impedance value, the controller 152 operates at a high speed to provide pulse signals by the controller 152 to the H bridge portion 158. When the output of the pin 164 is grounded because the capacitor 162 effectively is in parallel with the capacitor 160 the controller slows down for the delay period. Alternating the controller speed between high and low greatly conserves the energy available from the battery 86. The current supplied to the capacitors 160 and 162 through the output 164 preferably is kept small to increase the lifetime of the battery 86.

The pulse signals supplied to the H bridge circuit portion 158 are one of two inputs to the H bridge circuit portion 158. The output at 174 and 176 from the electronic controller 152 preferably is provided through capacitors 172 and 180, respectively. The arrangement of the capacitors 172 and 180 and the associated resistors forms a level shifter to control the P-channel FET. The level shifters provided by the capacitor and resistor arrangements accommodate the needed voltage differential to properly operate the P-channel FET. Since the electronic controller 152 preferably is a 5 volt microprocessor, the level shifter arrangements are utilized to achieve the voltage differential on the order of 3 or 4 volts required for the desired operation of the H bridge circuit portion 158.

A pulse width modulated voltage regulator circuit portion 190 also provides an input to the H bridge circuit portion 158. The signal from the output 192 preferably is a pulse width modulated signal. The duty cycle of the open collector pulse output from 192 determines the voltage that is provided from the voltage regulator circuit portion 190 to the H bridge circuit portion 158. The voltage regulator circuit portion 190 develops a variable voltage in the range from approximately 2 to 9 volts depending on the output from 192. This relatively wide variation in voltage at the output of the voltage regulator circuit portion 190 is accomplished even though the controller 152 preferably is a 5 volt microprocessor. The resulting signals provided from the circuitry 150 through the leads 50 preferably are amplitude controlled, monophasic, square wave pulses having alternating polarity. In the preferred embodiment, the pulse signals provided by the circuitry 150 are voltage regulated and transformer coupled utilizing a transformer 194. The preferred embodiment of the transformer 194 includes utilizing an injection molding process to separate the primary and secondary windings of the transformer coil. This provides the ability to satisfy the I.E.C. 601 safety standard and still make the transformer 194 relatively smaller, which enhances the ability to place all of the circuitry 150 on a single circuit board 80 and to fit all of the circuit components within a relatively small housing 30. The preferred embodiment includes a housing 30 that effectively fits within a palm of a person's hand.

This invention preferably includes a specially designed transformer 194 so that there is no DC path of current to allow the tube used during surgery. The I.E.C. 601 safety standard requires isolation of the leads 50 from the battery power source. It is not possible to have a DC source available directly at the leads 50 and still allow the device to be used during surgery. This invention addresses that particular need in a unique manner.

The 601 safety standard typically would require an 8 millimeter spacing between the two windings of the transformer 194. A transformer of this size could not be accommodated in a hand-held device, such as the preferred embodiment of this invention. The transformer 194 preferably includes the primary winding set upon a plastic bobbin and encased entirely in plastic. The primary winding preferably is sealed entirely within a layer of plastic. The second winding is placed over the plastic that encases the first winding. The layer of plastic sealing in the primary winding provides the necessary isolation so that the preferred embodiment of this invention satisfies the 601 safety standard.

An alternative to the plastic encased primary winding includes putting a capacitor in series with both output leads 56 and using a generic transformer as the transformer 194. The preferred embodiment of this invention includes the uniquely designed transformer described above.

Additionally, the preferred embodiment of this invention includes effectively clamping the primary winding of the transformer 194 to ground whenever no active pulse is provided by the electronics 150.

The preferred embodiment also includes an open lead detection circuit, which comprises an opto-isolator circuit portion 196. When both of the leads 50 are appropriately connected to pads 24 through the connectors 56 (or 56 and 59) and the pads are electrically coupled with the patient, current is permitted to flow through the secondary winding of the transformer 194. The opto-isolator preferably is bi-directional and placed in series with the leads 50 to monitor the current flowing through the secondary transformer winding. The light emitting diodes 198 of the opto-isolator 196 only generate light when current flows through that portion of the circuit. The photo transistor 200 responds to the light from the light emitting diodes 198 resulting in a change in the state of the output of the transistor 200.

The electronic controller 152 preferably monitors the state of the output of the transistor 200 to determine whether both of the leads 50 are appropriately connected with wires 58 and that the corresponding pads 24 are placed on the patient to conduct the stimulating signals to the patient's muscles. If the state of the transistor 200 indicates an open circuit or connection, the controller 152 causes an alarm indication, preferably causing the indicators 44 to flash. At the same time, the electronic controller 152 will not permit operation of the device. This open lead detection circuitry provides isolation needed for IEC 601 between the patient and the electronics 150 and minimizes any amount of time the device is used with a broken/disconnected circuit with the patient.

The electronics of this invention preferably also include a unique arrangement of LED's 44. In a typical scenario, eight different LED's would be powered utilizing eight different outputs of a microprocessor. This invention preferably includes an arrangement as illustrated so that only five outputs from the controller 152 are required to control all eight LED's. The pattern of providing power from the five outputs determines the pattern of which of the LED's are turned on. The electronic controller 152 preferably includes a look up table that gives the various patterns for providing energy through the five dedicated outputs. Given this description and the illustration of FIG. 9, those skilled in the art will be able to develop an appropriate look up table or to otherwise program the controller 152 to achieve a desired lighting pattern depending on the needs so of a particular situation.

SYSTEM FUNCTION

In the preferred embodiment, one electrode pad 24 is placed on each calf of the patient. Providing only a single electrode to each limb of the patient presents an advantage compared to many prior art devices because it utilizes less components, makes application of the system to the patient less complicated and more general, non-focused muscle contractions result. The electrode pads 24 preferably include an adhesive, conductive gel that adheres to the patient's skin and conducts the pulse signals from the stimulator device 22 into the patient's muscle fibers.

The system of this invention preferably elicits non-discrete muscle fiber activation so that the patient's muscles "twitch" in response to the electrical stimulation from the system 20. The term "twitch" is used in this specification to refer to a single triggering of the neuro-muscular junction by a short pulse of electrical current. Importantly, the electrically stimulated muscle is allowed to relax before a subsequent electrical current stimulation is provided to the neuro-muscular junction. The twitch elicited by the system 20 effectively simulates naturally occurring twitches of skeletal muscles.

Inducing muscle twitch is preferred to inducing muscle tetany, which is typically caused by multiple triggerings of a neuro-muscular junction in rapid enough succession that the stimulated muscle does not have time to relax between the individual contractions. In tetany, the contractions build in strength and generate torques that are typically three or four times in amplitude compared to those generated by a single twitch stimulation using identically sized and shaped electrical pulses. Tetanic contractions that are held for any appreciable length of time are felt by the patient as a muscle cramp or "charlie horse."

When tetany contractions of a single muscle group are not paired with concurrent tetany contractions of opposing muscle groups, the result is movement of a patient's limbs. The system of this invention employs muscle twitch rather than muscle tetany contractions to enhance patient comfort. Moreover, the utilization of muscle twitch presents a significant advantage in that the system of this invention can be used in an intra-operative setting because the patient's limbs remain relatively still as is typically required during surgery.

Muscle twitch, without tetany, is accomplished by controlling the frequency of the pulsed stimulation signals provided through the electrode pads 24.

This invention utilizes a series of pulses having a controlled duration time with a delay time between each pulse that is at least approximately 1000 times as long as the duration time. A desirable range for the duration time is between about 100 and 400 microseconds. A desired range for the delay time is between about 100 and 400 milliseconds. In the preferred embodiment, each series includes eight pulses each having a 200 microseconds duration that are provided in succession with 200 milliseconds delays between each signal. At the end of the eight pulses, the system preferably pauses for approximately 43.4 seconds and then repeats the series of eight pulses.

A patient or medical professional is able to adjust the amplitude or intensity of the stimulation signals utilizing the up and down adjustment buttons 40 and 42. Although the maximum stimulating intensity is controllable by the user, the eight pulses preferably do not all have the same amplitude or intensity. Instead, the electronic controller 152 preferably generates the first of the eight pulses with 40% of the current setting for the stimulation amplitude. The second, third, fourth and fifth pulses each preferably include a 15% increase in amplitude compared to the previous pulse. The fifth through the eighth pulses all preferably have 100% or full strength amplitude based upon the current stimulation setting chosen by a patient or medical professional.

By providing pulses of a 200 microsecond duration with 200 milliseconds between pulses, muscle twitch is accomplished while avoiding muscle tetany. Therefore, the system 20 of this invention is useful from the inception of a surgical procedure through the complete recovery period, including home care, to prevent the formation of DVT's. A system designed according to this invention assists in preventing DVT formation during and immediately after surgery, which studies have shown is the optimal time for intervention.

The simplicity and mobility provided by the system designed according to this invention permits a patient to utilize the system at home throughout the recovery period as directed by a medical professional. Additionally, there is no limitation on using a system designed according to this invention to situations where the patient must remain seated or lying down. The system designed according to this invention will typically not interfere with a patient's sleep since no significant limb movement results from the twitches induced by the system.

The electronic controller 152 preferably is programmed to provide the series of electrical pulses having the frequency to ensure the instigation of muscle twitch without causing muscle tetany. Additionally, the electronic controller 152 preferably causes the indicators 44 to light up to provide a visible indication of the operation of the device 22. For example, for each 200 microsecond pulse, the indicators 44 preferably are energized by a 25 millisecond pulse. The LED from the row of indicators 44 which is lit preferably corresponds to the amplitude or value of the current stimulation setting.

While the device is operating, the electronic controller 152 preferably monitors the operation of the up and down switches 132 and 134, respectively. During the 43.4 second pause, if the up button is depressed, the electronic controller 152 adjusts the stimulation setting and the stimulator 22 outputs four pulses each with 200 microsecond durations. If the up button is still depressed after the four pulses, then the electronic controller 152 increases the stimulation setting and preferably causes the H bridge circuit portion to generate one pulse having a 200 microsecond duration. When a user continuously holds down the up button, the electronic controller 152 continues to provide single 200 microsecond pulses until the maximum intensity is reached or the up button is released.

A similar routine is followed upon detecting that the down button 134 has been depressed. When a desired stimulation setting or the maximum (or minimum) is reached, the electronic controller 152 controls the ensuing eight stimulation pulses at the chosen level until further adjustments are made.

During the pause after a series of eight pulses, the electronic controller 152 preferably also monitors the state of the transistor 170 to determine if an open lead is detected. Whenever an open lead is detected, the electronic controller 152 preferably lights up all of the indicators while monitoring the up and down switches 132 and 134. Whenever an open lead is detected, the stimulation setting preferably cannot be adjusted.

The electronic controller 152 preferably goes into a sleep mode upon alternating activations of the power switch 130. When activated, the electronic controller 152 monitors the status of the increase switch 132 to determine if it is stuck in an activated state. If the switch 132 is stuck, the electronic controller 152 remains in sleep mode. Additionally, during operation when the increase switch 132 is activated (i.e., held down) for more than thirty pulses when the maximum signal strength is reached, the electronic controller 152 preferably goes into the sleep mode. Additionally, the electronic controller 152 preferably is programmed to recognize when the device 22 has been turned on and left at the minimum setting for a period of one hour. At the end of the hour, the electronic controller 152 preferably automatically goes into sleep mode to conserve power.

Given this description, those skilled in the art will be able to choose from among commercially available circuit components to realize the electronics 150. Similarly, given this description, those skilled in the art will be able to suitably program a commercially available microprocessor to realize the intended operation and functions of the electronic controller 152.

This specification describes an example implementation of this invention. Variations and modifications may become apparent to those skilled in the art that do not necessarily depart from the purview and spirit of this invention. The scope of legal protection given to this invention can only be determined by the following claims.

The following is claimed:

1. A system for preventing the occurrence of deep vein thrombosis, comprising:
   a first electrode that is adapted to be placed on a selected portion of a patient's body;
   a second electrode that is adapted to be placed on another portion of the patient's body; and
   a stimulator device having a pulse generating portion that supplies a series of electrical pulses to the electrodes to stimulate the patient's muscles in the vicinity of the electrodes to cause muscle twitch without inducing tetanic muscle contractions;
   each pulse is a square wave and wherein each pulse has a polarity that is opposite from a polarity of a preceding pulse.

2. The system of claim 1, including an electronic controller that causes the pulse generating portion to generate the electrical pulses such that each pulse has a duration time and a delay time, said delay time separates each pulse in the series, with said delay time being approximately 1000 times the duration time.

3. The system of claim 2, wherein each series of pulses includes a first pulse and a last pulse and the electronic controller causes the signal generating portion to pause between the last pulse of one series of pulses and the first pulse of a subsequent series of pulses and wherein the pause has a pause time that is at least 15 times greater than a sum of the duration times and the delay times from each series of pulses.

4. The system of claim 3, wherein each series of pulses includes between five and ten pulses and wherein the duration time is in a range from approximately 100 microseconds to approximately 400 microseconds, and the delay time is in a range from approximately 100 milliseconds to approximately 400 milliseconds.

5. The system of claim 4, wherein the series of pulses includes between five and ten pulses, the duration time is approximately 200 microseconds and the delay time is approximately 200 milliseconds.

6. The system of claim 2, wherein the stimulator device includes a housing, a power source supported within the housing, at least one electrical connection terminal adapted to be connected to the power source and a circuit board that supports the electronic controller, the pulse generating portion and said at least one electrical connection terminal, and wherein the circuit board is supported by the housing to be in a first position where the electrical connection terminal does not make electrical contact with the power source before the housing is closed and a second position where the connection terminal makes electrical contact with the power source when the housing is closed.

7. The system of claim 6, wherein the housing includes a first housing portion and a second housing portion and wherein the power source is received within the housing between the circuit board and the first housing portion and wherein the second housing portion includes at least one biasing member that biases the circuit board toward the power source to make electrical contact between the connection terminal and the power source.

8. The system of claim 7, wherein the first and second housing portions are ultrasonically welded together.

9. The system of claim 6, wherein the circuit board is generally planar and the system further includes a lead and a connection member coupled to each of the electrodes and wherein the connection members are supported within the housing such that a portion of the connection members are generally coplanar with the circuit board when the circuit board is received within the housing.

10. The system of claim 7, wherein the circuit board is generally planar and made from a generally flexible material and wherein the circuit board flexes from the first position into the second position responsive to the biasing member on the second housing portion.

11. The system of claim 1, wherein the series of pulses has a first pulse with a first intensity, a second pulse with a second intensity that is greater than the first intensity, a third pulse with a third intensity that is greater than the second intensity, a fourth pulse with a fourth intensity that is greater than the third intensity and a fifth pulse with a fifth intensity that is greater than the fourth intensity.

12. The system of claim 11, wherein there is a user selected intensity and the first intensity is approximately 40% of the selected intensity, the second intensity is approximately 55% of the selected intensity, the third intensity is approximately 70% of the selected intensity, the fourth intensity is approximately 85% of the selected intensity and the fifth intensity is approximately equal to the selected intensity.

13. The system of claim 12, wherein the series of pulses has a total of eight pulses and the fifth, sixth, seventh and eighth pulses each have an intensity that is approximately equal to the selected intensity.

14. The system of claim 13, wherein the duration time is approximately 200 microseconds, the delay time is approximately 200 milliseconds and the pause time is approximately 40 seconds.

15. The system of claim 1, wherein the electrodes each include a conductive, adhesive gel that is adapted to be adhesively secured to the patient's skin.

16. The system of claim 15, wherein the electrodes are each placed on a calf of the patient in the vicinity of the gastrocnemius muscle and wherein the gel has a dimension that is sized to be greater than approximately 50% of a surface dimension of the patient's gastrocnemius muscle and the electrodes each include a waterproof backing that has a backing dimension that is greater than the gel dimension.

17. The system of claim 16, wherein the first electrode is the only electrode placed on the patient's left leg and the second electrode is the only electrode placed on the patient's right leg.

18. The system of claim 1, including a controller that continuously operates in either a first mode or a second mode, the first mode corresponding to the stimulator device supplying the series of electrical pulses and the second mode corresponding to the stimulator device not supplying any electrical pulses.

19. The system of claim 1, including a controller that is driven at first clock speed when the stimulator device provides an electrical pulse and a second clock speed during periods between pulses.

20. The system of claim 19, wherein the first clock speed is approximately ten times faster than the second clock speed.

21. The system of claim 19, including an oscillator circuit having a variable time constant that alternates the clock speed between the first clock speed and the second clock speed, the oscillator circuit time constant being changed when an input to the oscillator circuit alternates between a high impedance and a low impedance.

22. The system of claim 1, wherein the stimulator device includes a transformer having a primary winding and a secondary winding and wherein the primary and secondary windings are separated by an injection molded plastic.

23. The system of claim 1, wherein the stimulator device includes an open lead detection circuit that monitors current flowing through the electrodes and provides an indication when there is no current flowing through the electrodes.

24. The system of claim 23, including a controller that communicates with the open lead detection circuit and responds to an indication that no current is flowing through the electrodes by controlling the stimulator device to not provide pulses.

25. The system of claim 24, wherein the open lead detection circuit comprises an opto-oscillator.

26. The system of claim 1, wherein the stimulator device includes a plurality of light emitting diodes and a controller for controlling the diodes, the controller having a plurality of outputs for providing power to the diodes that are fewer in number than the diodes and the controller includes a look-up table that dictates an illumination pattern of the diodes.

27. The system of claim 1, including a housing for housing the stimulator and wherein the housing includes a belt clip that is received into a portion of the housing, the belt clip including cantilever snap arms that are received into the housing to securely lock the belt clip relative to the housing, the belt clip including a rigid tongue portion for carrying a load when the belt clip is in use.

28. A system for preventing the occurrence of deep vein thrombosis, comprising:
- a first electrode that is adapted to be placed on a selected portion of a patient's body;
- a second electrode that is adapted to be placed on another portion of the patient's body; and
- a stimulator device having a pulse generating portion that supplies a series of electrical pulses to the electrodes to stimulate the patient's muscles in the vicinity of the electrodes to cause muscle twitch without inducing tetanic muscle contractions;
- the series of pulses has a first pulse with a first intensity, a second pulse with a second intensity that is greater than the first intensity, a third pulse with a third intensity that is greater than the second intensity, a fourth pulse with a fourth intensity that is greater than the third intensity and a fifth pulse with a fifth intensity that is greater than the fourth intensity;
- wherein there is a user selected intensity and the first intensity is approximately 40% of the selected intensity, the second intensity is approximately 55% of the selected intensity, the third intensity is approximately 70% of the selected intensity, the fourth intensity is approximately 85% of the selected intensity and the fifth intensity is approximately equal to the selected intensity;
- the series of pulses has a total of eight pulses and the fifth, sixth, seventh and eighth pulses each have an intensity that is approximately equal to the selected intensity; and
- the duration time is approximately 200 microseconds, the delay time is approximately 200 milliseconds and the pause time is approximately 40 seconds.

29. A system for preventing the occurrence of deep vein thrombosis, comprising:
- a first electrode that is adapted to be placed on a selected portion of a patient's body;
- a second electrode that is adapted to be placed on another portion of the patient's body; and
- a stimulator device having a pulse generating portion that supplies a series of electrical pulses to the electrodes to stimulate the patient's muscles in the vicinity of the electrodes to cause muscle twitch without inducing tetanic muscle contractions; and
- a controller that is driven at a first clock speed when the stimulator device provides an electrical pulse and a second clock speed during periods between pulses.

30. The system of claim 29, wherein the first clock speed is approximately ten times faster than the second clock speed.

31. The system of claim 29, including an oscillator circuit having a variable time constant that alternates the clock speed between the first clock speed and the second clock speed, the oscillator circuit time constant being changed when an input to the oscillator circuit alternates between a high impedance and a low impedance.

32. A system for preventing the occurrence of deep vein thrombosis, comprising:
- a first electrode that is adapted to be placed on a selected portion of a patient's body;
- a second electrode that is adapted to be placed on another portion of the patient's body; and
- a stimulator device having a pulse generating portion that supplies a series of electrical pulses to the electrodes to stimulate the patient's muscles in the vicinity of the electrodes to cause muscle twitch without inducing tetanic muscle contractions;
- the stimulator device includes a transformer having a primary winding and a secondary winding and wherein the primary and secondary windings are separated by an injection molded plastic.

33. A system for preventing the occurrence of deep vein thrombosis, comprising:
- a first electrode that is adapted to be placed on a selected portion of a patient's body;
- a second electrode that is adapted to be placed on another portion of the patient's body; and
- a stimulator device having a pulse generating portion that supplies a series of electrical pulses to the electrodes to stimulate the patient's muscles in the vicinity of the electrodes to cause muscle twitch without inducing tetanic muscle contractions;
- the stimulator device includes an open lead detection circuit that monitors current flowing through the electrodes and provides an indication when there is no current flowing through the electrodes; and
- a controller that communicates with the open lead detection circuit and responds to an indication that no current is flowing through the electrodes by controlling the stimulator device to not provide pulses;
- wherein the open lead detection circuit comprises an opto-oscillator.

34. A system for preventing the occurrence of deep vein thrombosis, comprising:
- a first electrode that is adapted to be placed on a selected portion of a patient's body;
- a second electrode that is adapted to be placed on another portion of the patient's body; and
- a stimulator device having a pulse generating portion that supplies a series of electrical pulses to the electrodes to stimulate the patient's muscles in the vicinity of the electrodes to cause muscle twitch without inducing tetanic muscle contractions;
- the stimulator device includes a plurality of light emitting diodes and a controller for controlling the diodes, the controller having a plurality of outputs for providing power to the diodes that are fewer in number than the diodes and the controller includes a look-up table that dictates an illumination pattern of the diodes.

* * * * *